United States Patent [19]
Brickley

[11] Patent Number: 5,968,455
[45] Date of Patent: Oct. 19, 1999

[54] ULTRAVIOLET AIR STERILIZATION DEVICE AND MOBILE UNIT INCORPORATING STERILIZATION DEVICE

[76] Inventor: James Lawrence Brickley, 100 Ward Rd., Anaconda, Mont. 59711

[21] Appl. No.: 09/286,241

[22] Filed: Apr. 5, 1999

Related U.S. Application Data

[63] Continuation-in-part of application No. 09/024,698, Feb. 17, 1998, Pat. No. 5,902,552.

[51] Int. Cl.$^6$ ...................................................... A62B 7/08
[52] U.S. Cl. ................ 422/121; 250/455.11; 250/522.1; 362/267; 422/120
[58] Field of Search .................................... 422/120, 121, 422/4, 24; 250/455.11, 504 R, 522.1; 313/318.01, 318.08; 362/267; 15/246.3

[56] References Cited

U.S. PATENT DOCUMENTS

| | | | |
|---|---|---|---|
| 4,227,446 | 10/1980 | Sone et al. ............................... | 422/121 |
| 4,244,712 | 1/1981 | Tongret .................................... | 422/121 |
| 4,293,847 | 10/1981 | McCarty .............................. | 362/267 X |
| 4,786,812 | 11/1988 | Humphreys ........................ | 250/455.11 |
| 5,060,121 | 10/1991 | Cunningham et al. ............. | 363/267 X |
| 5,185,015 | 2/1993 | Searle ........................................ | 55/102 |
| 5,523,057 | 6/1996 | Mazzilli ................................. | 422/121 |
| 5,558,158 | 9/1996 | Elmore ................................... | 165/122 |
| 5,635,133 | 6/1997 | Glazman ................................. | 422/24 |
| 5,656,242 | 8/1997 | Morrow et al. ........................ | 422/121 |
| 5,902,552 | 5/1999 | Brickley ................................. | 422/121 |

Primary Examiner—Krisanne Thornton
Attorney, Agent, or Firm—Fields and Johnson, P.C.

[57] ABSTRACT

In a first aspect of the invention, an ultraviolet air sterilization device includes a housing and one or more mounts which connect to germicidal lamp units which protrude into the air stream of an air handling duct. Each lamp has an integral receptacle with an electrical connection for attachment to a source of power from within the housing. The receptacle/lamp combination provides stiffening reinforcement to the lamp. The receptacles connect to their corresponding mounts by means of a threaded connection which enables the lamp units to be easily removed from within the air handling duct. In a second aspect of the invention, a mobile ultraviolet sterilization is provided. The mobile ultraviolet sterilization device includes the sterilization device of the first aspect mounted to a mobile platform or frame. A handle is also provided enabling an operator to traverse the sterilization device over a floor covering at a desired speed.

8 Claims, 5 Drawing Sheets

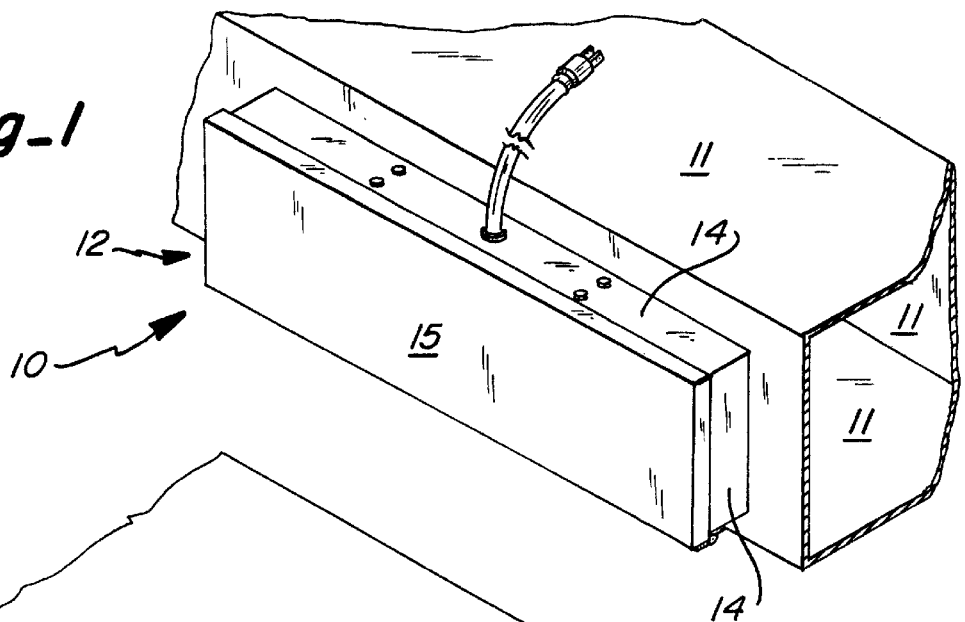
Fig_1
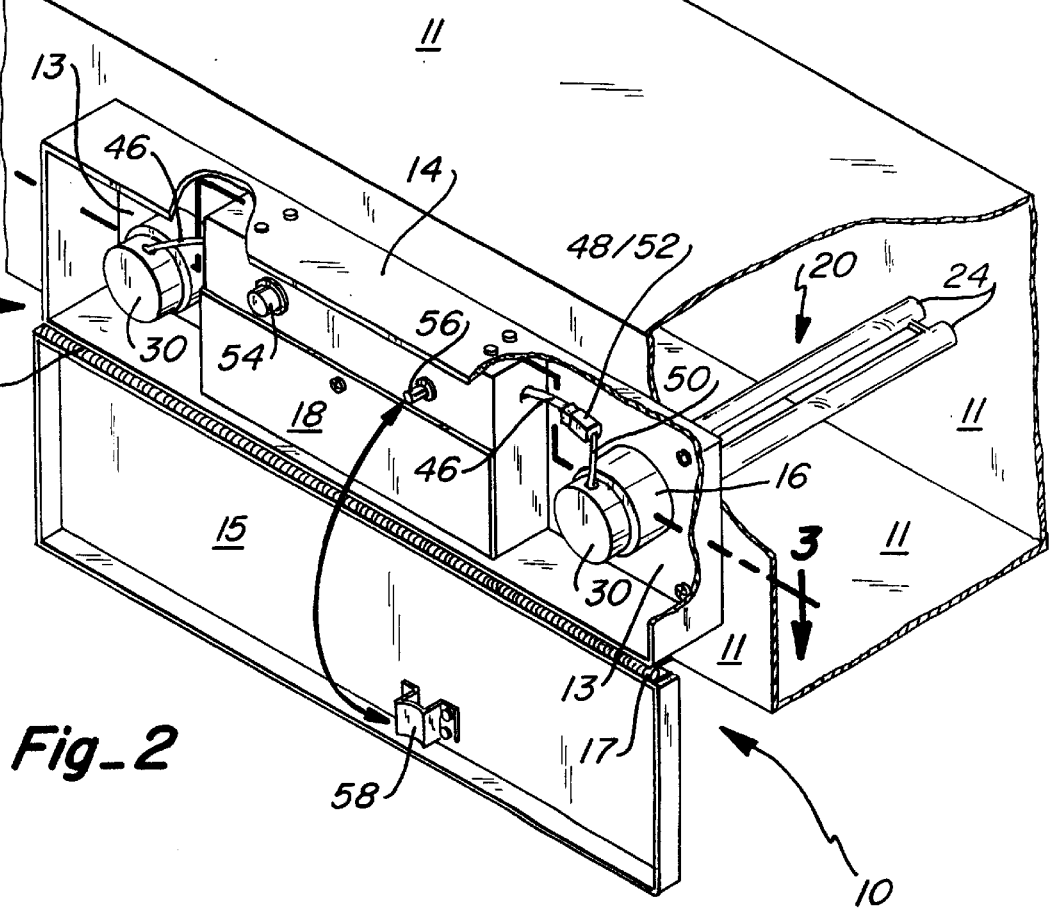
Fig_2

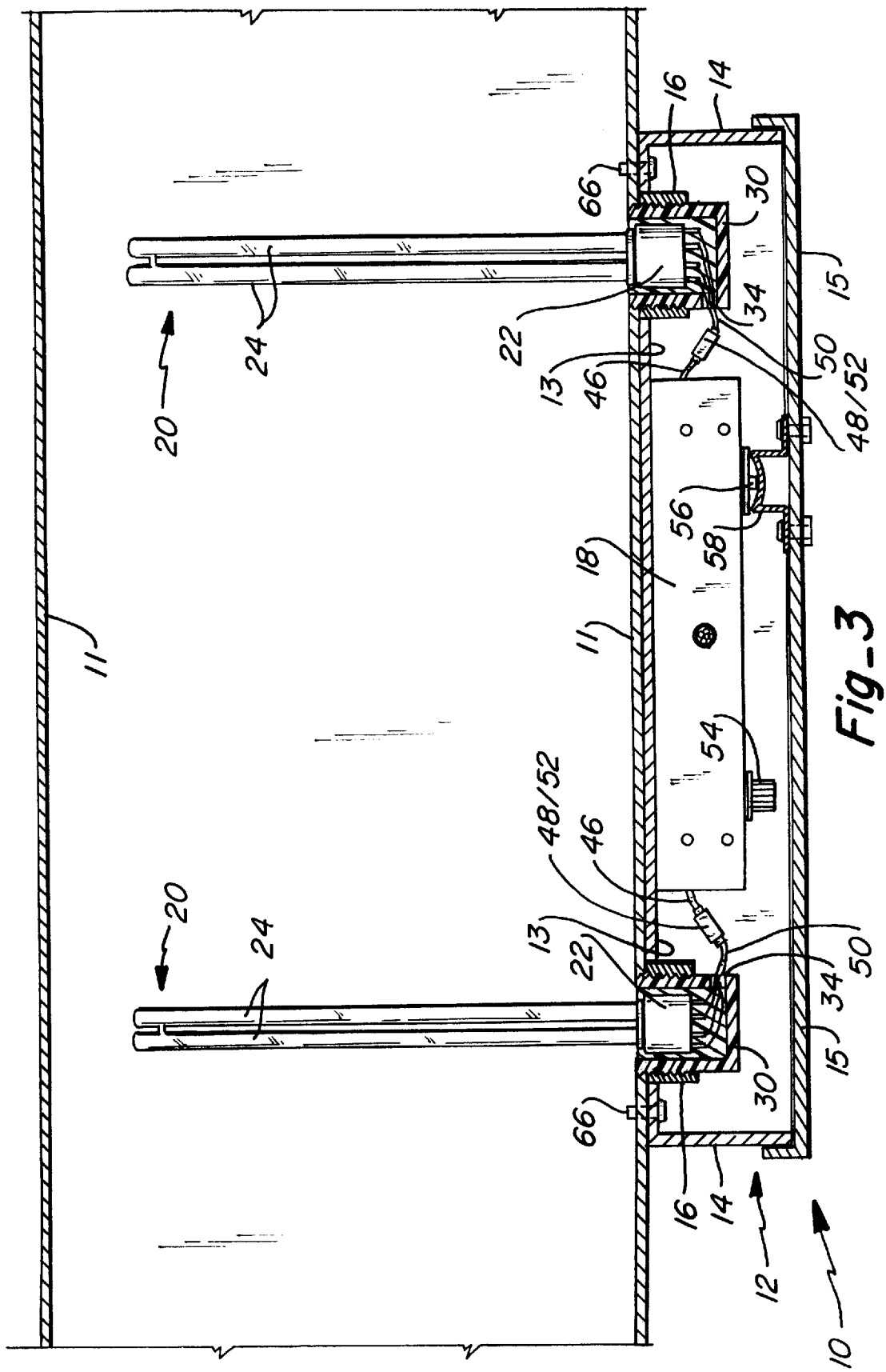
Fig_3

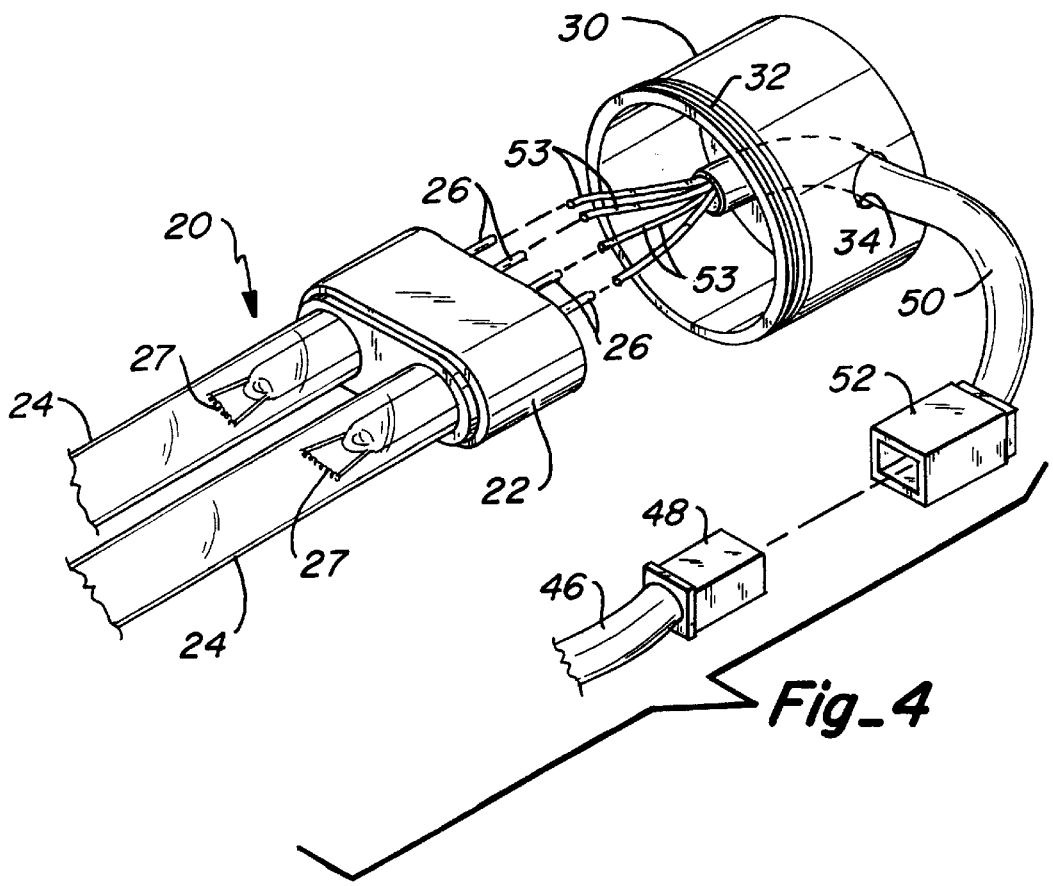
Fig_4
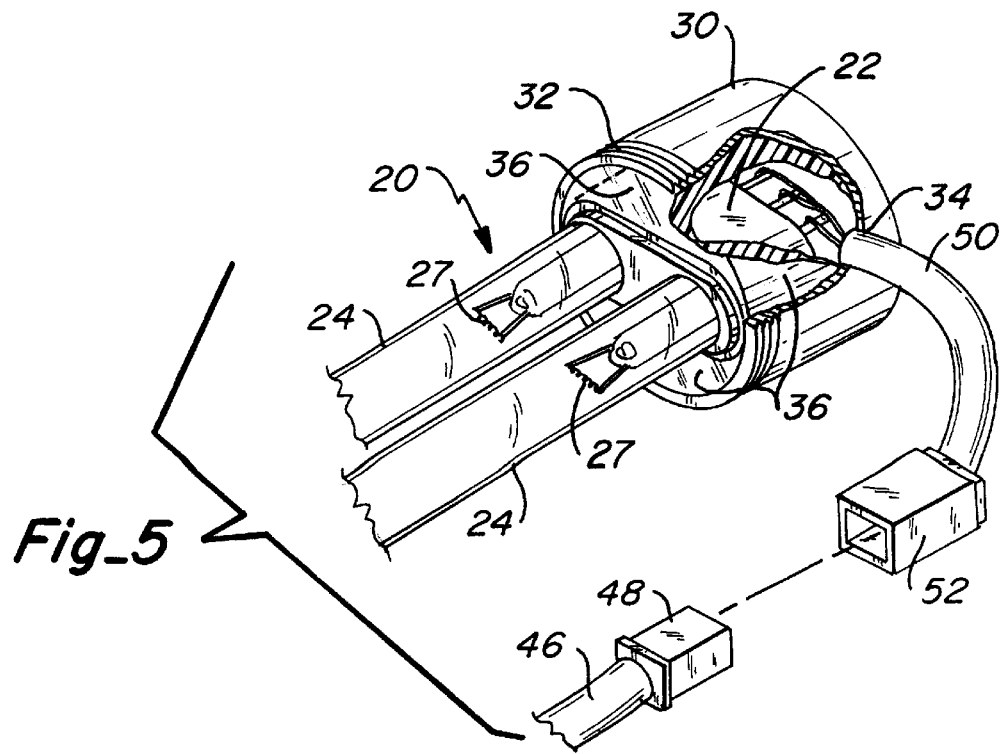
Fig_5

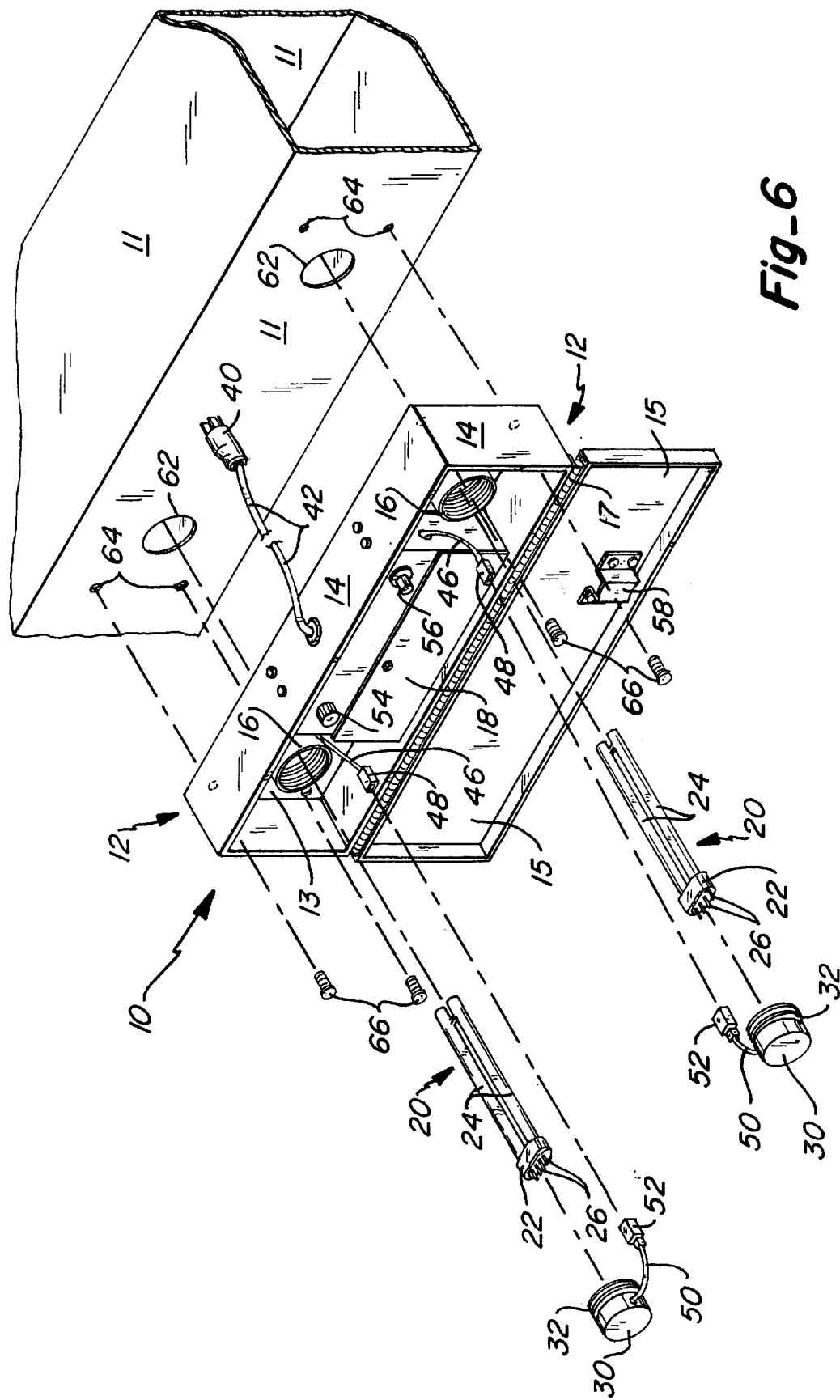
Fig_6

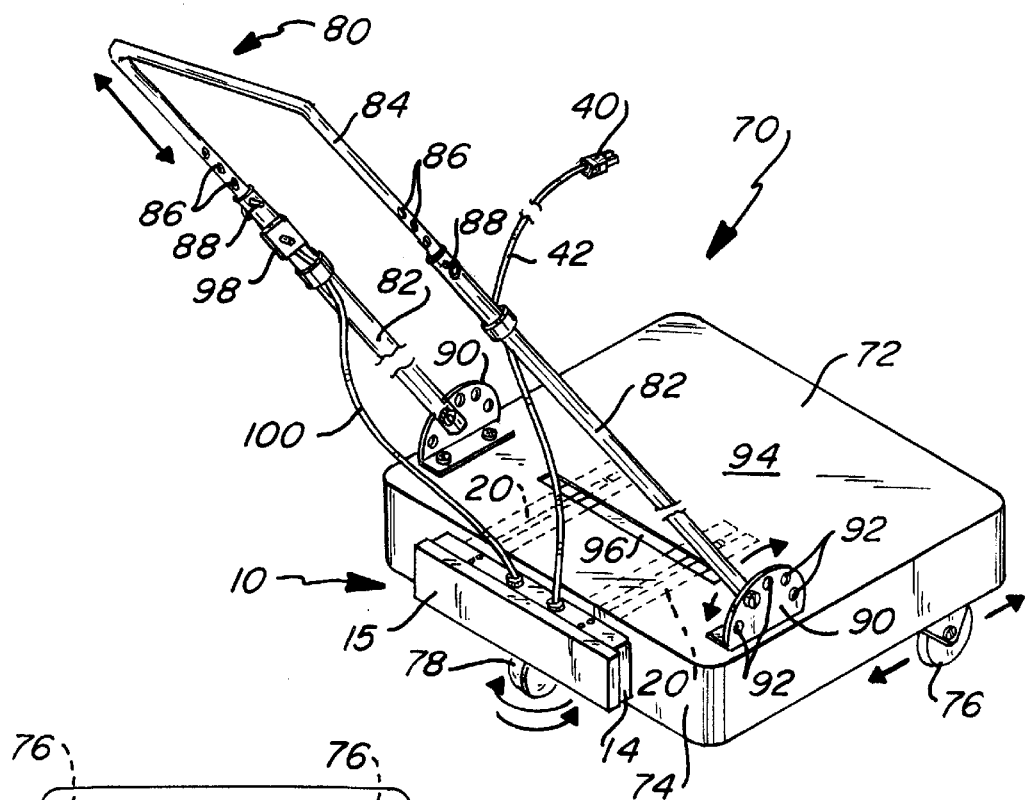
Fig_7
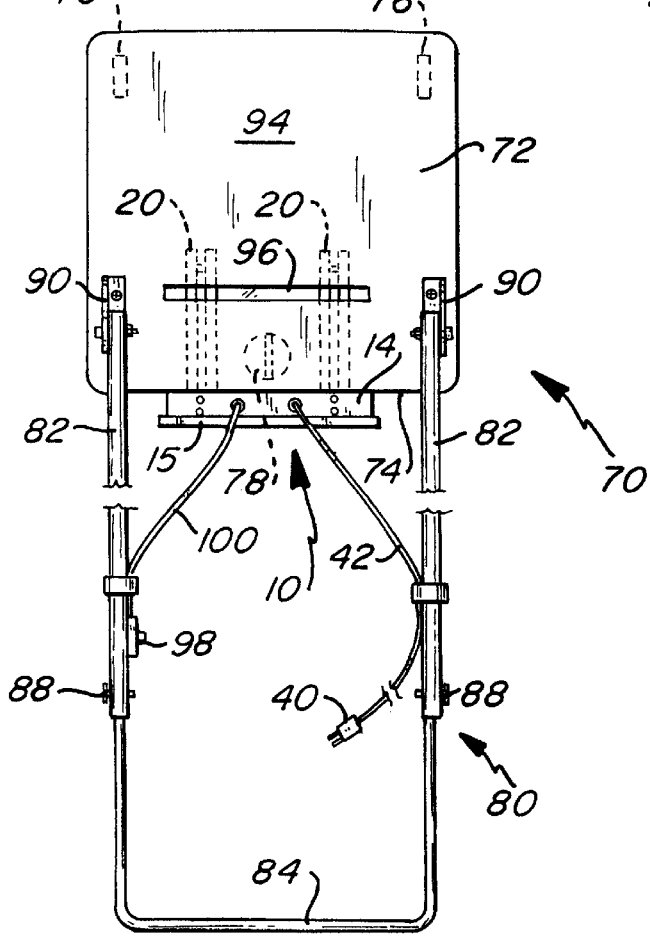
Fig_8

ULTRAVIOLET AIR STERILIZATION DEVICE AND MOBILE UNIT INCORPORATING STERILIZATION DEVICE

This application is a continuation-in-part application of U.S. Ser. No. 09/024,698 filed Feb. 17, 1998 and entitled "Ultraviolet Air Sterilization Device" now U.S. Pat. No. 5,902,552.

TECHNICAL FIELD

This invention relates to an improvement in an ultraviolet air sterilization device and, more particularly, to an improved air sterilization device which incorporates easily removable germicidal lamps of reinforced construction to withstand the high air velocities present in air handling units. The invention further relates to a mobile ultraviolet sterilization device to clean and disinfect floor coverings.

BACKGROUND ART

The use of an ultraviolet light source to kill bacteria and other microorganisms found in the air has been known for many years. In short, ultraviolet light is of a frequency which is able to effectively kill many types of microorganisms including bacteria and viruses. It is known to place ultraviolet light sources in an air stream in order to assist in the cleaning or sterilization of air introduced into a defined area. For example, it is known to place germicidal or ultraviolet lamps into the air stream of air handling units in order to clean and disinfect air which may be recirculated in an enclosed space. This cleaning or sterilization effect helps in reducing the contraction of bacterial or viral infections in closed air spaces such as offices which may not receive enough quantities of fresh air. Particularly in the winter months for colder climate areas, the introduction of fresh air into air handling units is greatly reduced in such colder months. Therefore, to alleviate the undue recirculation of contaminated air which may contain bacterial or viral agents, a complex set of filters along with ultraviolet lamps may be used.

One major problem with prior art devices which introduce a germicidal lamp directly into the air stream of an air handling unit is that the lamp receptacles which receive the lamps are not strong enough to withstand the continual bending stress created by high velocity air passing over the germicidal lamps. Accordingly, the bases of the lamps fracture or are otherwise damaged by the high velocity. The lamp receptacles themselves may also become damaged due to the continual stress. Over a period of time, the entire air sterilization device may need to be replaced because the lamp receptacles have been so damaged that they are no longer able to hold germicidal lamps.

Additionally, the high amount of dust and other particulate matter which passes through an air handling unit ultimately introduces these particles in the small gaps between the lamp receptacles and the base portions of the lamps. Because the lamps are not effectively sealed with respect to the lamp receptacles, the lamps often cannot be unscrewed from the receptacles which requires the entire sterilization device to be removed from the air handling unit.

Germicidal lamps, like all bulbs or lamps, need replacement over time as they burn out. Germicidal lamps particularly need to be cleaned periodically to remove dust and particulate buildup which form on the lamps. If such buildup is not removed, the ability of the ultraviolet light to penetrate the oncoming air stream is greatly diminished. However, most prior art devices require one to access the air handling unit interior in order to remove the lamps which makes bulb cleaning and replacement difficult.

In addition to the use of germicidal lamps in air streams of air handling units, such germicidal lamps also have utility with respect to killing microorganisms or undesirable pests found in floor coverings such as carpets and rugs. Just like air passing through an air handling unit, floor coverings provide environments for the growth of undesirable microorganisms or other pests. Germicidal lamps are effective in killing microorganisms to include dust mites and other pests.

SUMMARY OF THE INVENTION

In accordance with one aspect of the present invention, an ultraviolet air sterilization device is provided. In its simplest form, the device of this first aspect includes a housing which contains at least one lamp mount for receiving a germicidal lamp. Each lamp is reinforced in its construction by use of an integral lamp receptacle which is permanently bonded to the base portion of the corresponding lamp. Thus, each lamp and its receptacle form a single unit. The receptacle/lamp unit is easily removed from the housing by mounting it on a threaded connection with respect to a corresponding lamp mount. The base portion of each lamp is sealed with respect to its receptacle by means of a resin or other material.

A hole is cut in the air handling unit to allow the germicidal lamp to be placed in the air stream. The lamp mounts are preferably made of standard threaded conduit mounting flanges. The receptacles are made of a high strength plastic which is able to withstand high temperatures and bending stresses. The lamp mounts are positioned within the housing so that the lamps are the only portions of the device which protrude into the air flow. The use of the conduit mounting flanges and receptacles which are sealed with respect to the lamps greatly reinforce the lamps and their capability to withstand continuous stress. The receptacles are connected to a source of power by means of a quick connect/disconnect. If it is desired to clean or replace a germicidal lamp, an operator simply opens an access panel on the housing which allows access to the receptacle, disconnects the quick connect/disconnect, unscrews the receptacle from its threaded connection with the mount, and removes the lamp. Accordingly, there is no need to independently access the interior of the air handling unit to clean or replace the lamps.

In the preferred embodiment of the first aspect, there are two lamp mounts provided for mounting corresponding germicidal lamps to be placed into the air stream of an air handling unit. Each of the receptacle units has its own quick connect/disconnect connections.

The access panel or lid of the housing may include an interlock switch which shuts off power to the germicidal lamps when the access panel is open. A single rapid start ballast may be electrically connected to the receptacles in order to provide steady current to the germicidal lamps.

By use of the foregoing, germicidal lamps may be easily introduced into an air stream in a reinforced manner because of the construction of the receptacles which are rigidly attached to their corresponding lamps. Because the receptacles themselves are threadably mounted within the housing, the receptacle/lamp units may be easily removed for replacement or cleaning. The receptacle/lamp unit can be supplied as a replacement part wherein the base of the lamps are already sealed to the receptacle with the desired resin material. Each of these units would also include the quick connect/disconnect connection in order that the units can be connected to the existing wiring in the housing.

Each of the foregoing advantages of this invention are achieved with a relatively simple structure which may be manufactured and installed at a minimum cost.

In accordance with a second aspect of the present invention, a mobile ultraviolet sterilization device is provided. The housing and the elements therein are the same as in the first embodiment; however, the housing is mounted on a mobile unit which is able to effectively place the germicidal lamp in communication with floor coverings. In its simplest form, the preferred embodiment of this second aspect includes a carriage or frame for mounting the housing. The carriage or frame includes a plurality of casters which enables the germicidal lamp to traverse the floor covering. A handle connects to the carriage which enables the user to move the mobile unit over the floor covering at a desired rate. The preferred embodiment of the second aspect incorporates most of the advantages discussed above with respect to the first embodiment. For example, each lamp is reinforced in its construction by the use of an integral lamp receptacle which is permanently bonded to the base portion of the corresponding lamp. The lamp and its receptacle form a single unit which allows the receptacle/lamp unit to be easily removed from the housing. If it is desired to clean or replace a germicidal lamp, the operator simply opens the access panel on the housing which allows access to the receptacle. Therefore, there is no need to turn the mobile unit upside down or to otherwise access the underside of the carriage for lamp replacement.

In the preferred embodiment of the second aspect, there are two lamp mounts provided; however, it should be understood that this number may be increased or decreased depending upon the intensity of the light necessary to effectively treat microorganisms or other pests in the floor covering.

Additional advantages of this invention will become apparent from the description which follows, taken in conjunction with the accompanying drawings.

BRIEF DESCRIPTION OF THE DRAWINGS

FIG. 1 is a perspective view of the ultraviolet air sterilization device of this invention as mounted to an air duct incorporated within an air handling unit;

FIG. 2 is a fragmentary perspective view of the air sterilization device of this invention illustrating the lid or access panel open exposing the interior of the housing, and further illustrating one of the germicidal lamps as it is positioned within the duct;

FIG. 3 is a horizontal section, taken along line 3—3 of FIG. 2 illustrating the placement of the germicidal lamps within the air duct and further illustrating the reinforced construction of the receptacle/lamp units as such units are mounted within their corresponding mounts;

FIG. 4 is an exploded perspective view of a germicidal lamp prior to mounting within a corresponding receptacle;

FIG. 5 is a fragmentary perspective view of a germicidal lamp mounted within a corresponding receptacle wherein resin or other sealing material rigidly holds the lamp within the receptacle;

FIG. 6 is an exploded perspective view of the air sterilization device of this invention illustrating further structural details of the component parts;

FIG. 7 is a perspective view of the mobile ultraviolet sterilization device; and FIG. 8 is a plan view of the mobile ultraviolet sterilization device.

BEST MODE FOR CARRYING OUT THE INVENTION

FIG. 1 illustrates the ultraviolet air sterilization device 10 of the first aspect as mounted to the duct 11 of an air handling unit. The sterilization device 10 comprises a housing unit 12 characterized by a box-like structure having side panels 14, a lid or access panel 15, and as shown in FIG. 2, a rear panel 13 which mounts flush to the duct 11. As shown in FIG. 2, the lid or access panel 15 may simply be mounted about hinge 17. A pair of mounts 16 in the form of conduit mounting flanges are positioned at opposite ends of the housing 12 for receiving corresponding receptacles 30, as further explained below. A ballast and circuitry cover 18 may be provided within housing 12 for isolating the ballast (not shown) and the wiring which is used to provide power to the germicidal lamps 20.

As shown in FIGS. 4 and 5, the germicidal lamps 20 each include a lamp base 22 and a lighting element 24 which is illuminated when provided with an electrical power source. A plurality of pin connections 26 transfer electrical power to the lamp filaments 27 housed within the lighting elements 24. Each of the germicidal lamps 20 are mounted in corresponding receptacles 30. Receptacles 30 may be constructed of a UL approved plastic material with external threads 32 which enable the receptacles to be threadably mounted to the mounts 16. The mounts 16 may be constructed of standard 2" electrical conduit with an internal threaded end to receive a corresponding receptacle 30.

Referring to FIGS. 4 and 5, each receptacle 30 has an opening 34 for receiving a transfer cable 50 which comprises a plurality of wires 53 which are connected to pins or terminals 26 on base 22 as by a soldered connection. As shown in FIG. 5, the lamp base 22 is secured within its receptacle by means of a casting resin 36. Resin 36 fills the opening in receptacle 30 and is flush with the interface between base 22 and element 24.

Referring to FIG. 6, a grounded power supply plug 40 with cord 42 may be used as the connection for a source of power to be provided to the sterilization device 10. As will be understood by those skilled in the art, the cord 42 provides power to the ballast (not shown) which, in turn, provides a steady electrical current to the receptacles 30. Power is transferred from the ballast through transfer cables 46 to transfer cables 50 of each of the receptacles 30. The free ends of cables 46 and 50 include quick connect/disconnect couplers 48 and 52, respectively.

The circuitry of the air sterilization device 10 includes a fuse 54 which can handle any over current loading. Additionally, a safety shut-off switch 56 is provided to shut-off current flowing the receptacles 30 when the lid 15 is open. Switch 56 is in a normally open position when the lid is opened. When the lid is closed, switch trigger 58 causes the switch 56 to close thus allowing current to flow to the receptacles 30.

As shown in FIG. 6, when it is desired to mount the air sterilization device 10 to the duct 11, two openings 62 are drilled in the duct wall of a size which may receive the germicidal lamps 20. The housing 12 is mounted to the duct by a plurality of sheet metal screws 66 which are threadably received in screw holes 64 in the side wall of duct 11.

Referring back to FIG. 3, it can be seen that dust or other particulate matter is prevented from entering the housing 12 because the mounts 16 are flush against the duct wall and the holes 62 are sized to not exceed the diameter of the receptacles 30.

The housing 12 may be constructed of galvanized metal which is resilient to oxidation from exposure to moisture or other corrosive elements. An appropriate ballast for providing the desired current to the lamps is a 120 volt, 0.3 amp rapid start ballast. Additionally, a 2 amp fuse may be used which will prevent damage to most germicidal lamps. One recommended type of germicidal lamp that may be used in this invention is manufactured by Phillips, Model TUV PL-L (18 watt) long life germicidal lamp.

Although this preferred embodiment illustrates two germicidal lamps introduced within a duct, it shall be understood that the housing of this invention may be modified to include more or less lamps depending upon the needed ultraviolet saturization to sterilize a particular air flow. Additionally, it shall be understood that the germicidal lamps may be oriented within the air stream at a desired angle or position which best saturates the air flowing through that particular portion of the air handling unit. In some circumstances, it may be most effective to place the lamps in a transverse position as shown in FIG. 3. However, in other circumstances it may be desirable to reorient the lamps so they extend in a more parallel manner with respect to the direction of air flow.

By the foregoing, it is apparent that a simple structure is provided to enable the placement of germicidal lamps within an air duct. Because of the unitary construction of combining the receptacle 30 with the standard germicidal lamps 20, the germicidal lamps are much more capable of withstanding the high velocity and pressures associated with air flowing through an air handling unit. Accordingly, the lamps will remain in a rigid position within the air stream without damage occurring to either the lamps or to their mounts 16 within the housing. If it is necessary to replace or clean the lamps, the quick connects/disconnects are disconnected, and the receptacles are simply unscrewed from their mounts 16. If the germicidal lamp is burned out, it is replaced by another unit including a lamp and receptacle combination. Dust and other particulate matter which may normally clog sterilization devices used in air handling units is drastically reduced by sealing the lamps to their receptacles by means of a resin and by placing the mounts flush against the duct wall. Additionally, the threaded connection between the receptacles 30 and their corresponding mounts further reduces any migration of dust or other particulate matter into the housing 12.

In accordance with a second aspect of the invention, a mobile ultraviolet sterilization device 70 is provided. As shown in FIG. 7, the mobile device includes a carriage or frame 72 on to which the sterilization device 10 is mounted. More specifically, device 10 is mounted to the rear vertical wall 74 of the carriage 72. The device 10 is mounted to rear wall 74 in the same manner that the device 10 is mounted to the duct 11 in the first embodiment. The carriage 72 includes a pair of forward casters 76 and a free wheeling rear caster 78. The germicidal lamps 20 extend within the interior of the carriage 72 and substantially parallel to the surface of the floor covering traversed by the device 70. An operator may push the device 70 by means of handle 80. Handle 80 may include a lower portion 82 and an upper telescoping portion 84. A plurality of holes 86 formed in upper telescoping portion 84 allow the handle 80 to be adjusted to the desired height. Wing nuts 88 may be used to secure upper and lower portions 82 and 84. The lower ends of lower portion 82 attach to the carriage/frame 72 by means of corresponding flanges 90. As shown in FIG. 7, flanges 90 may include a plurality of arcuately spaced holes 92 which allow the lower handle portion 82 to be positioned at more vertical or horizontal positions.

The upper surface 94 of carriage/frame 72 may include a viewing port in the form of a slit or opening 96 which enables a user to review the germicidal lamps. The opening 96 may be covered with a clear plastic covering. The opening is provided simply to allow one to check that the lamps are operating. In lieu of an opening 96, any other well known visual means for checking the function of the lamps may be used. A remote "on/off" switch 98 electrically communicates with the ballast of the sterilization device 10 by cord or conductor 100. The use of the remote switch 100 is used in conjunction with the safety shutoff switch 56. Thus, the germicidal lamps are shut off when the lid 15 is opened, or an operator may manually energize or de-energize the lamps by switch 98.

In summary, the mobile ultraviolet sterilization device 70 is simply a mobile platform with the sterilization device 10 mounted thereto which enables the germicidal lamps to pass over floor coverings in order to achieve cleaning or sterilization of the floor covering. Since the sterilization device 10 is placed on a mobile platform, an operator may selectively choose the duration and location of applying the light rays emitted from the germicidal lamps.

This invention has been described in detail with reference to the particular embodiments hereof, but it will be understood that various other modifications can be effected within the spirit and scope of this invention.

I claim:

1. A mobile ultraviolet sterilization device comprising:

a housing;

a conduit mounting attached to said housing;

a receptacle removably mounted to said conduit mounting;

a lamp fixedly mounted to said receptacle so that said lamp is placed adjacent to a floor covering to expose the floor covering to light emitted from said lamp, said lamp including a lamp base;

a resin material placed in said receptacle and surrounding said lamp base to fixedly mount said lamp in said receptacle;

means for providing electrical power to said lamp;

a carriage for mounting said housing thereto;

a plurality of wheels attached to said carriage enabling said carriage to be traversed over the floor covering; and a handle attached to said carriage.

2. A device, as claimed in claim 1, further comprising:

a remote switch electrically communicating with said lamp to selectively energize or de-energize said lamp.

3. A device, as claimed in claim 1, further comprising:

means for adjusting an angle at which said handle attaches to said carriage.

4. A device, as claimed in claim 1, further comprising:

means for adjusting a height of said handle extending above said carriage.

5. A device, as claimed in claim 1, wherein:

said lamp extends from said housing substantially parallel to the floor covering.

6. A mobile ultraviolet sterilization device comprising:

a housing;

a lamp including a lamp base;

means for fixedly receiving said lamp including a resin material surrounding said lamp base;

means for removably mounting said lamp receiving means attached to said housing;

means for providing electrical power to said lamp;

a carriage for mounting said housing thereto;

a plurality of wheels attached to said carriage enabling said carriage to be traversed over a floor covering; and a handle attached to said carriage.

7. A device, as claimed in claim 6, wherein:

said means for providing electrical power to said lamp includes a quick connect/disconnect enabling said means for fixedly receiving said lamp to be electrically separated from or connected to said means for removably mounting.

8. A mobile ultraviolet sterilization device which helps to sanitize an exposed floor covering, in which the device includes at least one germicidal lamp placed adjacent the floor covering, the improvement comprising:

a housing;

a conduit mounting attached to said housing;

a receptacle removably mounted to said conduit mounting, the lamp being fixedly mounted to said receptacle so that the lamp is placed adjacent the floor covering to expose the floor covering to light emitted from the lamp;

a resin material placed in said receptacle and surrounding the lamp to fixedly mount the lamp in said receptacle;

means for providing electrical power to the lamp;

a carriage for mounting said housing thereto;

a plurality of wheels attached to said carriage enabling said carriage to be traversed over the floor covering; and a handle attached to said carriage.

* * * * *